(12) United States Patent
Delbac et al.

(10) Patent No.: US 6,890,536 B2
(45) Date of Patent: May 10, 2005

(54) MICROSPORIDIAN POLAR TUBE PROTEINS, NUCLEIC ACIDS CODING FOR THESE PROTEINS AND THEIR APPLICATIONS

(75) Inventors: Frédéric Delbac, Clermont-Ferrand (FR); Christian Vivares, Clermont-Ferrand (FR); Antoine Danchin, Paris (FR)

(73) Assignee: Centre National de la Recherche Scientifique—CNRS

( * ) Notice: Subject to any disclaimer, the term of this patent is extended or adjusted under 35 U.S.C. 154(b) by 0 days.

(21) Appl. No.: 09/755,456

(22) Filed: Jan. 5, 2001

(65) Prior Publication Data

US 2001/0021512 A1 Sep. 13, 2001

Related U.S. Application Data

(63) Continuation of application No. PCT/FR99/01630, filed on Jul. 6, 1999.

(30) Foreign Application Priority Data

Jul. 7, 1998 (FR) ............................................ 98/08692

(51) Int. Cl.[7] ...................... A61K 39/00; A61K 39/002; A61K 39/38; C07K 1/00
(52) U.S. Cl. ................................ 424/184.1; 424/185.1; 424/191.1; 424/265.1; 424/266.1; 530/350
(58) Field of Search .......................... 424/184.1, 185.1, 424/191.1, 265.1, 266.1; 530/300, 350

(56) References Cited

FOREIGN PATENT DOCUMENTS

WO    WO 98/02745    1/1998

OTHER PUBLICATIONS

Plotkin et al (*Vaccines* W.B. Saunders Co. Philadelphia p. 571), 1988.*
*First Complete Amino Acid Sequence of a Polar Tube Protein in a Microsporidian Species, Encephalitozoon Cuniculi*, Frédéric Delbac et al., The Journal of Eukaryotic Microbiology, vol. 44, No. 6, 1997, p. 77S.
*Immunocytochemical Identifiation of Spore Proteins in Two Microsporidia, with Emphasis on Extrusion Apparatus*, F. Delbac et al., Journal of Eukaryotic Microbiology, vol. 45, No. 2, (Apr. 1998), pp. 224–231.
*Identification of Sporal Proteins in two Microsporidian Species: an Immunoblotting and Immunocytochemical Study*, F. Delbac et al., The Journal of Eukaryotic Microbiology, vol. 43, No. 5, 1996, p. 101S.
*Identification of a Microsporidian Polar Tube Protein Reactive Monoclonal Antibody*, Elaine M. Keohane et al., The Journal of Eukaryotic Microbiology, vol. 43, No. 1, 1996, pp. 26–31.
*Detection of Microsporidia Spore–Specific Antigens by Monoclonal Antibodies*, H.D. Luján et al., Hybridoma, vol. 17, No. 3, (Jun. 1998), pp. 237–243.
*Utility of Microsporidian rRNA in Diagnosis and Phylogeny: a Review*, L.M. Weiss et al., Folia Parasitologica, vol. 41, 1994, pp. 81–90.
*Direct Amplification and Species Determination of Microsporidian DNA From Stool Specimens*, S. Katzwinkel–Wladarsch et al., Tropical Medicine and International Health, vol. 1, No. 3, (Jun. 1, 1996), pp. 373–378.
*Mapping of Repetitive and Non–Repetitive DNA Probes to Chromosomes of the Microsporidian Encephalitozoon cuniculi*, Corinne Biderre et al., GENE: An International Journal on Genes and Genomes, vol. 191, No. 1, (May 20, 1997), pp. 39–45.
*The Molecular Characterization of the Major Polar Tube Protein Gene from Encephalitozzon Hellem, a Microsporidian Parasite of Humans*, Elaine M. Keohane et al., Molecular and Biochemical Parasitology, vol. 94, (Aug. 1998), pp. 227–236.
*On Proteins of the Microsporidian Invasive Apparatus: Complete Sequence of a Polar Tube Protein of Encephalitozoon cuniculi*, Frédéric Delbac et al., Molecular Microbiology, vol. 29, No. 3, (Aug. 1998), pp. 825–834.

* cited by examiner

Primary Examiner—Mark Navarro
(74) Attorney, Agent, or Firm—DLA Piper Rudnick Gray Cary US LLP

(57) ABSTRACT

This invention discloses purified complete microsporidian polar tube proteins and the proteins, the amino acid sequences of which are represented in the attached sequence listings as SEQ ID No: 1, SEQ ID No: 2, SEQ ID No: 3, SEQ ID No: 4, SEQ ID No: 5. The invention discloses the genes coding these proteins and their use in the fields of diagnosis.

4 Claims, 5 Drawing Sheets

SEQUENCE LISTING

```
<160> NUMBER OF SEQ ID NOS: 10

<210> SEQ ID NO 1
<211> LENGTH: 1830
<212> TYPE: DNA
<213> ORGANISM: Encephalitozoon cuniculi
<220> FEATURE:
<221> NAME/KEY: CDS
<222> LOCATION: (345)..(1529)

<400> SEQUENCE: 1
gaattcagat gcctcatacc ttgggattaa aaaattgatg ttcatttgtt atatatcctg      60
ggcggacagg ccggctcgta ttcttcaggg gtgtcgccta cccagtgcac aggaggttcc     120
ggaggtgtct tggatggaaa gtaaggccat ttgtgggttc tcatccatgt catcgtccct     180
ttcggctgtt tcaccaagat ccaattattc ctccaggact ttcaaccctc agaatggaaa     240
cagagatgaa actctctgtg caaatcgtag atatcgattg gagacattga aaccacggag     300
```

-continued

| | |
|---|---|
| tttgaaataa aagtataaat acctccgaaa acgcagagtt taag atg aaa ggt att<br>                                Met Lys Gly Ile<br>                                 1 | 356 |
| tct aag atc ctc tct gcc tct att gcc ctg atg aag ttg gag aat gtc<br>Ser Lys Ile Leu Ser Ala Ser Ile Ala Leu Met Lys Leu Glu Asn Val<br> 5            10           15          20 | 404 |
| tat tca gca acc gca ctg tgc agc aat gca tat ggc cta act ccg gga<br>Tyr Ser Ala Thr Ala Leu Cys Ser Asn Ala Tyr Gly Leu Thr Pro Gly<br>        25            30            35 | 452 |
| caa cag ggt atg gct cag cag ccg tcg tat gtg ctg atc ccc agc acc<br>Gln Gln Gly Met Ala Gln Gln Pro Ser Tyr Val Leu Ile Pro Ser Thr<br>         40           45          50 | 500 |
| ccg gga acc ata gca aac tgt gca agc ggt tca cag gac aca tat tct<br>Pro Gly Thr Ile Ala Asn Cys Ala Ser Gly Ser Gln Asp Thr Tyr Ser<br>       55           60           65 | 548 |
| cct tct ccc gct gca ccc aca tct cca gtg act ccg ggg aaa act agc<br>Pro Ser Pro Ala Ala Pro Thr Ser Pro Val Thr Pro Gly Lys Thr Ser<br>70            75           80 | 596 |
| gag aat gag aca tct cca tcg gct cct gca gaa gat gta gga aca tgc<br>Glu Asn Glu Thr Ser Pro Ser Ala Pro Ala Glu Asp Val Gly Thr Cys<br>85            90          95          100 | 644 |
| aag att gcc gta ttg aag cac tgc gac gca cca gga aca aca tca ggg<br>Lys Ile Ala Val Leu Lys His Cys Asp Ala Pro Gly Thr Thr Ser Gly<br>          105           110          115 | 692 |
| acg aca cca ggg tca ggg cct tgt gaa acc cca gag cag caa cag cct<br>Thr Thr Pro Gly Ser Gly Pro Cys Glu Thr Pro Glu Gln Gln Gln Pro<br>         120           125          130 | 740 |
| ttg tca gtg atc tcc acc act cct gcc gta ccg gtg act gtg gag tct<br>Leu Ser Val Ile Ser Thr Thr Pro Ala Val Pro Val Thr Val Glu Ser<br>         135           140          145 | 788 |
| gca cag tct cca tct gtt gtg cca gtt gtt cct gtc gtt gct cac cac<br>Ala Gln Ser Pro Ser Val Val Pro Val Val Pro Val Val Ala His His<br>   150           155           160 | 836 |
| cag gca gtt cca ggc tac tac aac aat gga aca tcc ggt att cct gga<br>Gln Ala Val Pro Gly Tyr Tyr Asn Asn Gly Thr Ser Gly Ile Pro Gly<br>165           170           175          180 | 884 |
| cag caa cag atc ctt tct ggc act ctt ccc cca gga gcc act ttg tgt<br>Gln Gln Gln Ile Leu Ser Gly Thr Leu Pro Pro Gly Ala Thr Leu Cys<br>         185           190          195 | 932 |
| cag gga cag gcc atg cct agc act cct gga cag caa cag atc ctt tct<br>Gln Gly Gln Ala Met Pro Ser Thr Pro Gly Gln Gln Gln Ile Leu Ser<br>       200           205          210 | 980 |
| ggc act ctt ccc cca ggg gtc act ttg tgt cag gga cag gcc acg cct<br>Gly Thr Leu Pro Pro Gly Val Thr Leu Cys Gln Gly Gln Ala Thr Pro<br>    215          220           225 | 1028 |
| agc act cct ggg cag caa cag gtc ctt tct ggc act ctt ccc cca gga<br>Ser Thr Pro Gly Gln Gln Gln Val Leu Ser Gly Thr Leu Pro Pro Gly<br>230           235           240 | 1076 |
| gtc act ttg tgt cag gga cag gcc acg cct agc act cct ggg cag caa<br>Val Thr Leu Cys Gln Gly Gln Ala Thr Pro Ser Thr Pro Gly Gln Gln<br>245           250           255          260 | 1124 |
| cag gtc ctt tct ggc acc ctt ctc cca gga gcc act ttg tgt cag gat<br>Gln Val Leu Ser Gly Thr Leu Leu Pro Gly Ala Thr Leu Cys Gln Asp<br>         265           270          275 | 1172 |
| caa ggt atg cct gga aca tcc gga gtt cct gga cag cag gga cag tct<br>Gln Gly Met Pro Gly Thr Ser Gly Val Pro Gly Gln Gln Gly Gln Ser<br>       280           285          290 | 1220 |
| agt gga cag tgt tgt gcc cct cag att cca aac cct gtc atg ccg cca<br>Ser Gly Gln Cys Cys Ala Pro Gln Ile Pro Asn Pro Val Met Pro Pro<br>    295          300          305 | 1268 |

-continued

```
tcc atg aac att agt gga aat ggg tat cct tct tct acc gca tac agc      1316
Ser Met Asn Ile Ser Gly Asn Gly Tyr Pro Ser Ser Thr Ala Tyr Ser
    310                 315                 320 cca aac ctc gga tca ctg gga tcc tgt gtt gac ata cag aag acg ggg      1364
Pro Asn Leu Gly Ser Leu Gly Ser Cys Val Asp Ile Gln Lys Thr Gly
325                 330                 335                 340 ggg aca tcc tgc gag caa aaa ccc gag aag tcc gcc acg cag tat gcc      1412
Gly Thr Ser Cys Glu Gln Lys Pro Glu Lys Ser Ala Thr Gln Tyr Ala
                345                 350                 355 atg gag gcc tgt gca aca cca aca cca acg gtt att ata ggc aac agc      1460
Met Glu Ala Cys Ala Thr Pro Thr Pro Thr Val Ile Ile Gly Asn Ser
            360                 365                 370 gag tat ctt gtt gga cca gga atg tac aat gca att aac tct cca tgc      1508
Glu Tyr Leu Val Gly Pro Gly Met Tyr Asn Ala Ile Asn Ser Pro Cys
        375                 380                 385 aac act gct gtc caa tgc tgc taggctaaaa taaaacgagt ttaatcttct         1559
Asn Thr Ala Val Gln Cys Cys
    390                 395 ttttcttcgg tctttggaa cgttggatgg ggatggagga gtctatgggc tgaagtgaaa    1619
tgccaacact tcttctgccc aagaacacat tcggatgttc ttcctgtggc caggagtttg   1679
gtaacaggat tccccgagga tttagcagcc ttggagtacc atgattgaat cagtattaaa   1739
cttctcaaat tattttattc tttctgtttt atatcccgag ccaatctgag aagaatgcct   1799
cgaattcaag ctcccttaga agtgtgggat c                                  1830

<210> SEQ ID NO 2
<211> LENGTH: 1740
<212> TYPE: DNA
<213> ORGANISM: Encephalitozoon cuniculi
<220> FEATURE:
<221> NAME/KEY: CDS
<222> LOCATION: (458)..(1288)

<400> SEQUENCE: 2
aagcttctga caagcgcta accctctttc agaatatata aagcaatcca tacaacttct      60
ccatccatcc cggtgctgtt tctttggagg caaaacagag gaggtggcga tatcgatggt    120
gcatccataa tatatacaag acactccagg ctgcaactga atcaacacac tccatcccct    180
caggaagtcg gtaaacttgc cttgaaaata gccaatggat gtctccaggc tttataccat    240
gcacagctat atcttggcct gaagtgcact ttcaggtggg gctttgttac attgcggtgt    300
tttggattac ctgatataat tgttaccca ctgagtcaag tcgaaaccag tagtccgcag    360
atttctaaca gagaggaaag actggaggta atttgtggct tttgaaacat gcacagcaaa    420
ataaaatata aagaagcct tttgcacact accaaag atg ttg tta ctt ctc gcc     475
                                         Met Leu Leu Leu Leu Ala
                                           1               5 ata act gct gtt gtt agc gcc acg atg gtc cat cct tca gct gtt gtt      523
Ile Thr Ala Val Val Ser Ala Thr Met Val His Pro Ser Ala Val Val
         10                  15                  20 cca cag ccc gca gca cct ctc cat gtc gtt ccc cca cag cag caa atg      571
Pro Gln Pro Ala Ala Pro Leu His Val Val Pro Pro Gln Gln Gln Met
     25                  30                  35 ggc atg gtt aac gga tgc acc agc aag aaa cta gag ggt gca gaa ata      619
Gly Met Val Asn Gly Cys Thr Ser Lys Lys Leu Glu Gly Ala Glu Ile
 40                  45                  50 atg aga agg aac atg att gag tgc cag aaa aga agc tcg gag gca aca      667
Met Arg Arg Asn Met Ile Glu Cys Gln Lys Arg Ser Ser Glu Ala Thr
 55                  60                  65                  70
```

```
aag gcg atg att gaa agg gca aat gaa aag gct gta gaa tca ttc aac      715
Lys Ala Met Ile Glu Arg Ala Asn Glu Lys Ala Val Glu Ser Phe Asn
             75                  80                  85 aag gaa gtt agc aaa gga cct agc caa aag gat gga ggc cag tgc ata      763
Lys Glu Val Ser Lys Gly Pro Ser Gln Lys Asp Gly Gly Gln Cys Ile
         90                  95                 100 gaa aaa gct gta caa ggt acc gat agg tgt att ctc gct gga ata atc      811
Glu Lys Ala Val Gln Gly Thr Asp Arg Cys Ile Leu Ala Gly Ile Ile
        105                 110                 115 gat aag gcg gtg aac aag cgc aag tac aga atc tca gat gtg gag aac      859
Asp Lys Ala Val Asn Lys Arg Lys Tyr Arg Ile Ser Asp Val Glu Asn
    120                 125                 130 agc acc tcg ctc tac aga gga gac aag cta att gcc cta att gtc aat      907
Ser Thr Ser Leu Tyr Arg Gly Asp Lys Leu Ile Ala Leu Ile Val Asn
135                 140                 145                 150 gtc gac tat ggg ctg cag ccg atc act aag cca aag aag aag aag tcc      955
Val Asp Tyr Gly Leu Gln Pro Ile Thr Lys Pro Lys Lys Lys Lys Ser
                155                 160                 165 aag ata atg gcg aat ctc cct cag ccg aag aga gag atg tat ttc aac     1003
Lys Ile Met Ala Asn Leu Pro Gln Pro Lys Arg Glu Met Tyr Phe Asn
            170                 175                 180 caa atc ggt cag ctt gtt gga gca aga gga acg ttc ccc cag gaa aac     1051
Gln Ile Gly Gln Leu Val Gly Ala Arg Gly Thr Phe Pro Gln Glu Asn
        185                 190                 195 aag gag gac tgc aag cct tgt gag ggt ccc aag aag act gtt gaa act     1099
Lys Glu Asp Cys Lys Pro Cys Glu Gly Pro Lys Lys Thr Val Glu Thr
    200                 205                 210 act tct gag aaa tgt aat ctt ggg tgc gag ctt aaa gga aca tct gct     1147
Thr Ser Glu Lys Cys Asn Leu Gly Cys Glu Leu Lys Gly Thr Ser Ala
215                 220                 225                 230 ctg ata agc aag gcc ata cag aag aag gaa gtc aag gac acg aag gaa     1195
Leu Ile Ser Lys Ala Ile Gln Lys Lys Glu Val Lys Asp Thr Lys Glu
                235                 240                 245 ggg gag aaa agt gca agc cag gac tct gat ggc gag ggc act gct gag     1243
Gly Glu Lys Ser Ala Ser Gln Asp Ser Asp Gly Glu Gly Thr Ala Glu
            250                 255                 260 gat gcg gaa gta cag caa cct tct gcg gac ggc gag ggt cta gag         1288
Asp Ala Glu Val Gln Gln Pro Ser Ala Asp Gly Glu Gly Leu Glu
        265                 270                 275 taattttaa attaaaatct ccctggattg aatcttcaag tgcttttgtg aaagactttg   1348
ggaacatttc gtgaaggcta acataaattg ttaatctcag gtcactcgat ggaatagtca   1408
attcgtattt cctttccttg gatggtctgc cccaccagcc tgttcctggc agttatcgca   1468
tcgtcgacag agtcaaactg aacgaatcca tatcctttgg acatcttctt gtattggtcg   1528
tagactatta ctacccgata gttcagtatc tcactgatcc tctccttgag aaggtctcta   1588
acgtcgtctt cggttatgtg tgctcccagc ccaaatatcc ctatcgccct ggagggagac   1648
ccgtttctct ttgctttaag tgcatatctt tcgtttttat aggagcttgg atctgttcct   1708
tcgtatcccc ttgtcgggcg ctccacctcg ag                                1740

<210> SEQ ID NO 3
<211> LENGTH: 1116
<212> TYPE: DNA
<213> ORGANISM: Encephalitozoon intestinalis
<220> FEATURE:
<221> NAME/KEY: CDS
<222> LOCATION: (1)..(1113)

<400> SEQUENCE: 3
```

-continued

```
atg aaa ggt att tct aag gtt ctc tca gcc tct att gtc cta atg aag      48
Met Lys Gly Ile Ser Lys Val Leu Ser Ala Ser Ile Val Leu Met Lys
 1               5                  10                  15 ttg aag ggt gtc tat tct aca act gtg ctg tgt gga gat tca aca caa      96
Leu Lys Gly Val Tyr Ser Thr Thr Val Leu Cys Gly Asp Ser Thr Gln
            20                  25                  30 gga ctg cag ggc aca acc caa ccg tca tat gtg ctg gtt cct agt gca     144
Gly Leu Gln Gly Thr Thr Gln Pro Ser Tyr Val Leu Val Pro Ser Ala
        35                  40                  45 cca gag aca ata gcc aac tgt gga tac agt cca cag aac atg tat gtc     192
Pro Glu Thr Ile Ala Asn Cys Gly Tyr Ser Pro Gln Asn Met Tyr Val
    50                  55                  60 cct tct act cct act acc atg cct tcc aca gtg cca ggc aca act ggt     240
Pro Ser Thr Pro Thr Thr Met Pro Ser Thr Val Pro Gly Thr Thr Gly
65                  70                  75                  80 gag agc gag aca cct act tct cca aca tca tct cct aca gag gat gtg     288
Glu Ser Glu Thr Pro Thr Ser Pro Thr Ser Ser Pro Thr Glu Asp Val
                85                  90                  95 gga aca tgc aag att gct gtt gta aag cat tgt gat gca cca gga aca     336
Gly Thr Cys Lys Ile Ala Val Val Lys His Cys Asp Ala Pro Gly Thr
            100                 105                 110 tca tca aca cct tgc gaa ccg gaa cag act ttg gcc ccc tct cag cca     384
Ser Ser Thr Pro Cys Glu Pro Glu Gln Thr Leu Ala Pro Ser Gln Pro
        115                 120                 125 gta gca gct aca att gcc aca cca ctg gtt gtt gct tct gtg cag acg     432
Val Ala Ala Thr Ile Ala Thr Pro Leu Val Val Ala Ser Val Gln Thr
    130                 135                 140 ccg caa gca gct gtt acc atc ctt act cca aag gcc gtc tct gcc cag     480
Pro Gln Ala Ala Val Thr Ile Leu Thr Pro Lys Ala Val Ser Ala Gln
145                 150                 155                 160 ccg gca acc atc att tct cca ttc aac cag gca cca ggc tac tac aat     528
Pro Ala Thr Ile Ile Ser Pro Phe Asn Gln Ala Pro Gly Tyr Tyr Asn
                165                 170                 175 agt gca att ccc ggg caa ata ctt aca ggt aat gtt ctc tct cca agt     576
Ser Ala Ile Pro Gly Gln Ile Leu Thr Gly Asn Val Leu Ser Pro Ser
            180                 185                 190 gcc tct tct tgc caa gtg gtg ccc gga aca aca gga agc tcc acc ccc     624
Ala Ser Ser Cys Gln Val Val Pro Gly Thr Thr Gly Ser Ser Thr Pro
        195                 200                 205 cag cag cta cca ggc gct gtt tca tct gga acc att cct tgc caa ata     672
Gln Gln Leu Pro Gly Ala Val Ser Ser Gly Thr Ile Pro Cys Gln Ile
    210                 215                 220 gta cag gga act caa agt agc gga aac acc cct gga cag caa ttc ttg     720
Val Gln Gly Thr Gln Ser Ser Gly Asn Thr Pro Gly Gln Gln Phe Leu
225                 230                 235                 240 ccg gga atc gtt cct gtt gga agc ctc cag ccg gat caa gct act tct     768
Pro Gly Ile Val Pro Val Gly Ser Leu Gln Pro Asp Gln Ala Thr Ser
                245                 250                 255 gga acc cct acc cct tct gtt agc caa agc caa tct gga cag caa tgc     816
Gly Thr Pro Thr Pro Ser Val Ser Gln Ser Gln Ser Gly Gln Gln Cys
            260                 265                 270 tgc tgc act cct cca atc aca aac cct gta atg cca act cct atg ggt     864
Cys Cys Thr Pro Pro Ile Thr Asn Pro Val Met Pro Thr Pro Met Gly
        275                 280                 285 atc agc agt aat ggg tat ccc agc tca act gcg tac gcc cca acc ctt     912
Ile Ser Ser Asn Gly Tyr Pro Ser Ser Thr Ala Tyr Ala Pro Thr Leu
    290                 295                 300 gga caa ttg gga cct tgc atc gac aca cag aag tca aca tca tcc tgc     960
Gly Gln Leu Gly Pro Cys Ile Asp Thr Gln Lys Ser Thr Ser Ser Cys
```

```
                                    -continued
         305                310                315                320
gaa cca aaa gaa aag cct gta gca cag tat gga atg gaa gca tgc gct        1008
Glu Pro Lys Glu Lys Pro Val Ala Gln Tyr Gly Met Glu Ala Cys Ala
                    325                 330                335 gca cca act cca act gct gtt cta gga aat gct gag tat ctc ctt agc        1056
Ala Pro Thr Pro Thr Ala Val Leu Gly Asn Ala Glu Tyr Leu Leu Ser
                340                 345                 350 ccg ggg atg tat aat tca ctc aac tct cca tgc aac gct tgc tgc caa        1104
Pro Gly Met Tyr Asn Ser Leu Asn Ser Pro Cys Asn Ala Cys Cys Gln
            355                 360                 365 caa caa tgc tag                                                        1116
Gln Gln Cys
        370

<210> SEQ ID NO 4
<211> LENGTH: 828
<212> TYPE: DNA
<213> ORGANISM: Encephalitozoon intestinalis
<220> FEATURE:
<221> NAME/KEY: CDS
<222> LOCATION: (1)..(825)

<400> SEQUENCE: 4 atg ttg tta ctt ctc tca gca gtt gct ttt gtt agc gct aca gca gtc         48
Met Leu Leu Leu Leu Ser Ala Val Ala Phe Val Ser Ala Thr Ala Val
  1               5                  10                  15 cag tca ggt gtt gtc tcc cag cct aca aca ccc att ccg att ctt cct         96
Gln Ser Gly Val Val Ser Gln Pro Thr Thr Pro Ile Pro Ile Leu Pro
                 20                  25                  30 gga cag ccg atg ggg ggc atg gcc aac ggg tgc act aac aag aaa cta        144
Gly Gln Pro Met Gly Gly Met Ala Asn Gly Cys Thr Asn Lys Lys Leu
             35                  40                  45 gat ggt gtt gaa ata atg aga agg aac atg gtg gaa tgc cag aag aga        192
Asp Gly Val Glu Ile Met Arg Arg Asn Met Val Glu Cys Gln Lys Arg
         50                  55                  60 aat gca gag gca aca aaa gca atg gtt gaa agg gct aat gaa aag gct        240
Asn Ala Glu Ala Thr Lys Ala Met Val Glu Arg Ala Asn Glu Lys Ala
 65                  70                  75                  80 gta gaa aca ttc aat aag gag gtc agt aaa gga cct caa aag gaa agc        288
Val Glu Thr Phe Asn Lys Glu Val Ser Lys Gly Pro Gln Lys Glu Ser
                 85                  90                  95 ggc cag tgc ata gaa aaa gct gta cag ggc acc gac aga tgt att ctt        336
Gly Gln Cys Ile Glu Lys Ala Val Gln Gly Thr Asp Arg Cys Ile Leu
            100                 105                 110 gca gga ata att gat aag gct gtg aac aag cgt aag tac aga atc tcg        384
Ala Gly Ile Ile Asp Lys Ala Val Asn Lys Arg Lys Tyr Arg Ile Ser
        115                 120                 125 gat gtg gag aat agc acc tcg ctc tat aga ggc gac aaa cta att gct        432
Asp Val Glu Asn Ser Thr Ser Leu Tyr Arg Gly Asp Lys Leu Ile Ala
    130                 135                 140 cta att gtc aat gtt gac tat gga ctt cag cca att atc aaa cca aag        480
Leu Ile Val Asn Val Asp Tyr Gly Leu Gln Pro Ile Ile Lys Pro Lys
145                 150                 155                 160 aag aag aaa tcc aag ata atg gca aat ctt cct caa cca aag aga gag        528
Lys Lys Lys Ser Lys Ile Met Ala Asn Leu Pro Gln Pro Lys Arg Glu
                165                 170                 175 atg tat ttc aac cag atc gga cag ctt gtt gga gca aag gga aca ttc        576
Met Tyr Phe Asn Gln Ile Gly Gln Leu Val Gly Ala Lys Gly Thr Phe
            180                 185                 190 cct caa gac aac aag gat gaa tgc aag cca tgc gaa cct aag aag act        624
Pro Gln Asp Asn Lys Asp Glu Cys Lys Pro Cys Glu Pro Lys Lys Thr
```

-continued

```
              195                 200                 205
gtt gaa act gct tct gaa aga tgt aat ctt ggg tgc gag ctt aag gga     672
Val Glu Thr Ala Ser Glu Arg Cys Asn Leu Gly Cys Glu Leu Lys Gly
    210                 215                 220 acc tca gcc ctg ata agt aag gcc ata caa aag aag gag atc aag gag     720
Thr Ser Ala Leu Ile Ser Lys Ala Ile Gln Lys Lys Glu Ile Lys Glu
225                 230                 235                 240 agc cca aag gag ggg gac aga aac aca acc cag gaa tat gat ggt gag     768
Ser Pro Lys Glu Gly Asp Arg Asn Thr Thr Gln Glu Tyr Asp Gly Glu
                245                 250                 255 ggc tct gct gaa gat gct gaa ggc caa caa cct tct gca gac ggc gaa     816
Gly Ser Ala Glu Asp Ala Glu Gly Gln Gln Pro Ser Ala Asp Gly Glu
            260                 265                 270 ggt cta gag taa                                                     828
Gly Leu Glu
        275

<210> SEQ ID NO 5
<211> LENGTH: 819
<212> TYPE: DNA
<213> ORGANISM: Encephalitozoon hellem
<220> FEATURE:
<221> NAME/KEY: CDS
<222> LOCATION: (1)..(816)

<400> SEQUENCE: 5 atg ttg tta ctt ttc acc gta gtt act ctt gtt agc gct gca cag gtg     48
Met Leu Leu Leu Phe Thr Val Val Thr Leu Val Ser Ala Ala Gln Val
1               5                   10                  15 gca cct gta act ccg cag gca gct gta cct aca caa ttc ctt cct ggt     96
Ala Pro Val Thr Pro Gln Ala Ala Val Pro Thr Gln Phe Leu Pro Gly
            20                  25                  30 gcc cag caa aag att ggc ggt gtg gac aac aga tgt gcc aac aag caa     144
Ala Gln Gln Lys Ile Gly Gly Val Asp Asn Arg Cys Ala Asn Lys Gln
        35                  40                  45 gta gaa ggt gtt caa ata ttt caa gga gac atg gcc gat tgc ccg aaa     192
Val Glu Gly Val Gln Ile Phe Gln Gly Asp Met Ala Asp Cys Pro Lys
    50                  55                  60 aga aac tcc gag gct gca aat gca atg gtt caa aga gcc aag caa aag     240
Arg Asn Ser Glu Ala Ala Asn Ala Met Val Gln Arg Ala Lys Gln Lys
65                  70                  75                  80 gct tta gaa atc tac aat aag gag att agc aag ggc ccc aca cca aag     288
Ala Leu Glu Ile Tyr Asn Lys Glu Ile Ser Lys Gly Pro Thr Pro Lys
                85                  90                  95 gat agc ggc cag tgc ata gaa aga gct gta caa ggt act gac agg tgt     336
Asp Ser Gly Gln Cys Ile Glu Arg Ala Val Gln Gly Thr Asp Arg Cys
            100                 105                 110 att ctt gca aaa ata atc gac aag gct gtg aac atg ctt aag tac aga     384
Ile Leu Ala Lys Ile Ile Asp Lys Ala Val Asn Met Leu Lys Tyr Arg
        115                 120                 125 atc tca aag gta gga aat gct aca gca ctc ttc aga gga aac aag cta     432
Ile Ser Lys Val Gly Asn Ala Thr Ala Leu Phe Arg Gly Asn Lys Leu
    130                 135                 140 att tct cta att ctt aat gtt gat tat gga ctt aag cca ttc ttt act     480
Ile Ser Leu Ile Leu Asn Val Asp Tyr Gly Leu Lys Pro Phe Phe Thr
145                 150                 155                 160 gtt gta aag aag aaa aca aag aga gtg ttc ccc caa ggg gat gag ctg     528
Val Val Lys Lys Lys Thr Lys Arg Val Phe Pro Gln Gly Asp Glu Leu
                165                 170                 175 aac ttc aat gga att ggt cag ctt ata gga gta aaa ggc aca ttc cct     576
Asn Phe Asn Gly Ile Gly Gln Leu Ile Gly Val Lys Gly Thr Phe Pro
```

-continued

```
                180                 185                 190
caa gac aat aat gat gaa tgc aag ccg tgt gac tct cca aag aag act      624
Gln Asp Asn Asn Asp Glu Cys Lys Pro Cys Asp Ser Pro Lys Lys Thr
            195                 200                 205 gtt gag act gtt gct gag gaa tgt aat ctt ggg tgc cag ctt aag ggg      672
Val Glu Thr Val Ala Glu Glu Cys Asn Leu Gly Cys Gln Leu Lys Gly
    210                 215                 220 acg cct ggg ttg ata agc aga gcc ata caa aag aag gag gtc aag gaa      720
Thr Pro Gly Leu Ile Ser Arg Ala Ile Gln Lys Lys Glu Val Lys Glu
225                 230                 235                 240 agc tca aag gac gga gaa aaa agc tca acc cag aac ggc gaa ggc acc      768
Ser Ser Lys Asp Gly Glu Lys Ser Ser Thr Gln Asn Gly Glu Gly Thr
                245                 250                 255 acc gat gat gaa gat gga cag caa tct ccg gac ggt aat gga cca gag      816
Thr Asp Asp Glu Asp Gly Gln Gln Ser Pro Asp Gly Asn Gly Pro Glu
            260                 265                 270 taa                                                                  819
```

<210> SEQ ID NO 6
<211> LENGTH: 395
<212> TYPE: PRT
<213> ORGANISM: Encephalitozoon cuniculi

<400> SEQUENCE: 6

```
Met Lys Gly Ile Ser Lys Ile Leu Ser Ala Ser Ile Ala Leu Met Lys
  1               5                  10                  15

Leu Glu Asn Val Tyr Ser Ala Thr Ala Leu Cys Ser Asn Ala Tyr Gly
             20                  25                  30

Leu Thr Pro Gly Gln Gln Gly Met Ala Gln Pro Ser Tyr Val Leu
         35                  40                  45

Ile Pro Ser Thr Pro Gly Thr Ile Ala Asn Cys Ala Ser Gly Ser Gln
     50                  55                  60

Asp Thr Tyr Ser Pro Ser Pro Ala Ala Pro Thr Ser Pro Val Thr Pro
 65                  70                  75                  80

Gly Lys Thr Ser Glu Asn Glu Thr Ser Pro Ser Ala Pro Ala Glu Asp
                 85                  90                  95

Val Gly Thr Cys Lys Ile Ala Val Leu Lys His Cys Asp Ala Pro Gly
            100                 105                 110

Thr Thr Ser Gly Thr Thr Pro Gly Ser Gly Pro Cys Glu Thr Pro Glu
        115                 120                 125

Gln Gln Gln Pro Leu Ser Val Ile Ser Thr Thr Pro Ala Val Pro Val
    130                 135                 140

Thr Val Glu Ser Ala Gln Ser Pro Ser Val Val Pro Val Val Pro Val
145                 150                 155                 160

Val Ala His His Gln Ala Val Pro Gly Tyr Tyr Asn Asn Gly Thr Ser
                165                 170                 175

Gly Ile Pro Gly Gln Gln Ile Leu Ser Gly Thr Leu Pro Pro Gly
            180                 185                 190

Ala Thr Leu Cys Gln Gly Gln Ala Met Pro Ser Thr Pro Gly Gln Gln
        195                 200                 205

Gln Ile Leu Ser Gly Thr Leu Pro Gly Val Thr Leu Cys Gln Gly
    210                 215                 220

Gln Ala Thr Pro Ser Thr Pro Gly Gln Gln Gln Val Leu Ser Gly Thr
225                 230                 235                 240

Leu Pro Pro Gly Val Thr Leu Cys Gln Gly Gln Ala Thr Pro Ser Thr
                245                 250                 255
```

```
Pro Gly Gln Gln Gln Val Leu Ser Gly Thr Leu Leu Pro Gly Ala Thr
            260                 265                 270

Leu Cys Gln Asp Gln Gly Met Pro Gly Thr Ser Gly Val Pro Gly Gln
            275                 280                 285

Gln Gly Gln Ser Ser Gly Gln Cys Cys Ala Pro Gln Ile Pro Asn Pro
            290                 295                 300

Val Met Pro Pro Ser Met Asn Ile Ser Gly Asn Gly Tyr Pro Ser Ser
305                 310                 315                 320

Thr Ala Tyr Ser Pro Asn Leu Gly Ser Leu Gly Ser Cys Val Asp Ile
            325                 330                 335

Gln Lys Thr Gly Gly Thr Ser Cys Glu Gln Lys Pro Glu Lys Ser Ala
            340                 345                 350

Thr Gln Tyr Ala Met Glu Ala Cys Ala Thr Pro Thr Pro Thr Val Ile
            355                 360                 365

Ile Gly Asn Ser Glu Tyr Leu Val Gly Pro Gly Met Tyr Asn Ala Ile
            370                 375                 380

Asn Ser Pro Cys Asn Thr Ala Val Gln Cys Cys
385                 390                 395

<210> SEQ ID NO 7
<211> LENGTH: 277
<212> TYPE: PRT
<213> ORGANISM: Encephalitozoon cuniculi

<400> SEQUENCE: 7

Met Leu Leu Leu Ala Ile Thr Ala Val Val Ser Ala Thr Met Val
  1               5                  10                  15

His Pro Ser Ala Val Val Pro Gln Pro Ala Ala Pro Leu His Val Val
            20                  25                  30

Pro Pro Gln Gln Gln Met Gly Met Val Asn Gly Cys Thr Ser Lys Lys
            35                  40                  45

Leu Glu Gly Ala Glu Ile Met Arg Arg Asn Met Ile Glu Cys Gln Lys
 50                  55                  60

Arg Ser Ser Glu Ala Thr Lys Ala Met Ile Glu Arg Ala Asn Glu Lys
 65                  70                  75                  80

Ala Val Glu Ser Phe Asn Lys Glu Val Ser Lys Gly Pro Ser Gln Lys
            85                  90                  95

Asp Gly Gln Cys Ile Glu Lys Ala Val Gln Gly Thr Asp Arg Cys
            100                 105                 110

Ile Leu Ala Gly Ile Ile Asp Lys Ala Val Asn Lys Arg Lys Tyr Arg
            115                 120                 125

Ile Ser Asp Val Glu Asn Ser Thr Ser Leu Tyr Arg Gly Asp Lys Leu
130                 135                 140

Ile Ala Leu Ile Val Asn Val Asp Tyr Gly Leu Gln Pro Ile Thr Lys
145                 150                 155                 160

Pro Lys Lys Lys Ser Lys Ile Met Ala Asn Leu Pro Gln Pro Lys
            165                 170                 175

Arg Glu Met Tyr Phe Asn Gln Ile Gly Gln Leu Val Gly Ala Arg Gly
            180                 185                 190

Thr Phe Pro Gln Glu Asn Lys Glu Asp Cys Lys Pro Cys Glu Gly Pro
            195                 200                 205

Lys Lys Thr Val Glu Thr Thr Ser Glu Lys Cys Asn Leu Gly Cys Glu
            210                 215                 220

Leu Lys Gly Thr Ser Ala Leu Ile Ser Lys Ala Ile Gln Lys Lys Glu
```

```
                225                 230                 235                 240
Val Lys Asp Thr Lys Glu Gly Glu Lys Ser Ala Ser Gln Asp Ser Asp
                    245                 250                 255

Gly Glu Gly Thr Ala Glu Asp Ala Glu Val Gln Gln Pro Ser Ala Asp
                260                 265                 270

Gly Glu Gly Leu Glu
        275

<210> SEQ ID NO 8
<211> LENGTH: 371
<212> TYPE: PRT
<213> ORGANISM: Encephalitozoon intestinalis

<400> SEQUENCE: 8

Met Lys Gly Ile Ser Lys Val Leu Ser Ala Ser Ile Val Leu Met Lys
  1               5                  10                  15

Leu Lys Gly Val Tyr Ser Thr Thr Val Leu Cys Gly Asp Ser Thr Gln
                 20                  25                  30

Gly Leu Gln Gly Thr Thr Gln Pro Ser Tyr Val Leu Val Pro Ser Ala
             35                  40                  45

Pro Glu Thr Ile Ala Asn Cys Gly Tyr Ser Pro Gln Asn Met Tyr Val
         50                  55                  60

Pro Ser Thr Pro Thr Thr Met Pro Ser Thr Val Pro Gly Thr Thr Gly
 65                  70                  75                  80

Glu Ser Glu Thr Pro Thr Ser Pro Thr Ser Pro Thr Glu Asp Val
                 85                  90                  95

Gly Thr Cys Lys Ile Ala Val Val Lys His Cys Asp Ala Pro Gly Thr
                100                 105                 110

Ser Ser Thr Pro Cys Glu Pro Glu Gln Thr Leu Ala Pro Ser Gln Pro
            115                 120                 125

Val Ala Ala Thr Ile Ala Thr Pro Leu Val Val Ala Ser Val Gln Thr
        130                 135                 140

Pro Gln Ala Ala Val Thr Ile Leu Thr Pro Lys Ala Val Ser Ala Gln
145                 150                 155                 160

Pro Ala Thr Ile Ile Ser Pro Phe Asn Gln Ala Pro Gly Tyr Tyr Asn
                165                 170                 175

Ser Ala Ile Pro Gly Gln Ile Leu Thr Gly Asn Val Leu Ser Pro Ser
            180                 185                 190

Ala Ser Ser Cys Gln Val Val Pro Gly Thr Thr Gly Ser Ser Thr Pro
        195                 200                 205

Gln Gln Leu Pro Gly Ala Val Ser Ser Gly Thr Ile Pro Cys Gln Ile
    210                 215                 220

Val Gln Gly Thr Gln Ser Ser Gly Asn Thr Pro Gly Gln Gln Phe Leu
225                 230                 235                 240

Pro Gly Ile Val Pro Val Gly Ser Leu Gln Pro Asp Gln Ala Thr Ser
                245                 250                 255

Gly Thr Pro Thr Pro Ser Val Ser Gln Ser Gln Ser Gly Gln Gln Cys
            260                 265                 270

Cys Cys Thr Pro Pro Ile Thr Asn Pro Val Met Pro Thr Pro Met Gly
        275                 280                 285

Ile Ser Ser Asn Gly Tyr Pro Ser Ser Thr Ala Tyr Ala Pro Thr Leu
    290                 295                 300

Gly Gln Leu Gly Pro Cys Ile Asp Thr Gln Lys Ser Thr Ser Ser Cys
305                 310                 315                 320
```

-continued

Glu Pro Lys Glu Lys Pro Val Ala Gln Tyr Gly Met Glu Ala Cys Ala
            325                 330                 335

Ala Pro Thr Pro Thr Ala Val Leu Gly Asn Ala Glu Tyr Leu Leu Ser
            340                 345                 350

Pro Gly Met Tyr Asn Ser Leu Asn Ser Pro Cys Asn Ala Cys Cys Gln
        355                 360                 365

Gln Gln Cys
    370

<210> SEQ ID NO 9
<211> LENGTH: 275
<212> TYPE: PRT
<213> ORGANISM: Encephalitozoon intestinalis

<400> SEQUENCE: 9

Met Leu Leu Leu Ser Ala Val Ala Phe Ser Ala Thr Ala Val
 1               5                  10                 15

Gln Ser Gly Val Val Ser Gln Pro Thr Thr Pro Ile Pro Ile Leu Pro
            20                  25                  30

Gly Gln Pro Met Gly Met Ala Asn Gly Cys Thr Asn Lys Lys Leu
        35                  40                  45

Asp Gly Val Glu Ile Met Arg Arg Asn Met Val Glu Cys Gln Lys Arg
 50                  55                  60

Asn Ala Glu Ala Thr Lys Ala Met Val Glu Arg Ala Asn Glu Lys Ala
 65                  70                  75                  80

Val Glu Thr Phe Asn Lys Glu Val Ser Lys Gly Pro Gln Lys Glu Ser
                 85                  90                  95

Gly Gln Cys Ile Glu Lys Ala Val Gln Gly Thr Asp Arg Cys Ile Leu
            100                 105                 110

Ala Gly Ile Ile Asp Lys Ala Val Asn Lys Arg Lys Tyr Arg Ile Ser
        115                 120                 125

Asp Val Glu Asn Ser Thr Ser Leu Tyr Arg Gly Asp Lys Leu Ile Ala
    130                 135                 140

Leu Ile Val Asn Val Asp Tyr Gly Leu Gln Pro Ile Ile Lys Pro Lys
145                 150                 155                 160

Lys Lys Lys Ser Lys Ile Met Ala Asn Leu Pro Gln Pro Lys Arg Glu
                165                 170                 175

Met Tyr Phe Asn Gln Ile Gly Gln Leu Val Gly Ala Lys Gly Thr Phe
            180                 185                 190

Pro Gln Asp Asn Lys Asp Glu Cys Lys Pro Cys Glu Pro Lys Lys Thr
        195                 200                 205

Val Glu Thr Ala Ser Glu Arg Cys Asn Leu Gly Cys Glu Leu Lys Gly
    210                 215                 220

Thr Ser Ala Leu Ile Ser Lys Ala Ile Gln Lys Lys Glu Ile Lys Glu
225                 230                 235                 240

Ser Pro Lys Glu Gly Asp Arg Asn Thr Thr Gln Glu Tyr Asp Gly Glu
                245                 250                 255

Gly Ser Ala Glu Asp Ala Glu Gly Gln Gln Pro Ser Ala Asp Gly Glu
            260                 265                 270

Gly Leu Glu
    275

<210> SEQ ID NO 10
<211> LENGTH: 272
<212> TYPE: PRT
<213> ORGANISM: Encephalitozoon hellem -continued

<400> SEQUENCE: 10

```
Met Leu Leu Leu Phe Thr Val Val Thr Leu Val Ser Ala Ala Gln Val
  1               5                  10                  15

Ala Pro Val Thr Pro Gln Ala Ala Val Pro Thr Gln Phe Leu Pro Gly
             20                  25                  30

Ala Gln Gln Lys Ile Gly Gly Val Asp Asn Arg Cys Ala Asn Lys Gln
         35                  40                  45

Val Glu Gly Val Gln Ile Phe Gln Gly Asp Met Ala Asp Cys Pro Lys
     50                  55                  60

Arg Asn Ser Glu Ala Ala Asn Ala Met Val Gln Arg Ala Lys Gln Lys
 65                  70                  75                  80

Ala Leu Glu Ile Tyr Asn Lys Glu Ile Ser Lys Gly Pro Thr Pro Lys
                 85                  90                  95

Asp Ser Gly Gln Cys Ile Glu Arg Ala Val Gln Gly Thr Asp Arg Cys
            100                 105                 110

Ile Leu Ala Lys Ile Ile Asp Lys Ala Val Asn Met Leu Lys Tyr Arg
        115                 120                 125

Ile Ser Lys Val Gly Asn Ala Thr Ala Leu Phe Arg Gly Asn Lys Leu
    130                 135                 140

Ile Ser Leu Ile Leu Asn Val Asp Tyr Gly Leu Lys Pro Phe Phe Thr
145                 150                 155                 160

Val Val Lys Lys Lys Thr Lys Arg Val Phe Pro Gln Gly Asp Glu Leu
                165                 170                 175

Asn Phe Asn Gly Ile Gly Gln Leu Ile Gly Val Lys Gly Thr Phe Pro
            180                 185                 190

Gln Asp Asn Asn Asp Glu Cys Lys Pro Cys Asp Ser Pro Lys Lys Thr
        195                 200                 205

Val Glu Thr Val Ala Glu Glu Cys Asn Leu Gly Cys Gln Leu Lys Gly
    210                 215                 220

Thr Pro Gly Leu Ile Ser Arg Ala Ile Gln Lys Lys Glu Val Lys Glu
225                 230                 235                 240

Ser Ser Lys Asp Gly Glu Lys Ser Ser Thr Gln Asn Gly Glu Gly Thr
                245                 250                 255

Thr Asp Asp Glu Asp Gly Gln Gln Ser Pro Asp Gly Asn Gly Pro Glu
            260                 265                 270
```

MICROSPORIDIAN POLAR TUBE PROTEINS, NUCLEIC ACIDS CODING FOR THESE PROTEINS AND THEIR APPLICATIONS

RELATED APPLICATION

This is a continuation of International Application No. PCT/FR99/01630, with an international filing date of Jul. 6, 1999, which is based on French Patent Application No. 98/08692, filed Jul. 7, 1998.

FIELD OF THE INVENTION

This invention relates to purified complete microsporidian polar tube proteins (PTPs) as well as the genes coding these proteins and their use in the field of diagnosis.

BACKGROUND

*E. cuniculi* is a Microsporida, an obligate intracellular parasite, that occurs frequently in numerous mammals and is implicated in various infections in humans, principally in immunodepressed subjects. Two other species of the genus *Encephalitozoon* (*E. intestinalis* and *E. hellem*) are also implicated in various opportunistic infections. Generally speaking, the microsporidians are responsible in AIDS patients for gastrointestinal diseases, as well as ocular, muscular and hepatic disorders, rhinosinusitis and systemic infections [1]. Serological tests have also demonstrated the noteworthy presence of microsporidians in immunocompetent patients at the level of 8% of the population [2]. Four genera of microsporidians are responsible for human diseases: *Enterocytozoon, Encephalitozoon, Vittaforma* and *Trachipleistophora*. The emergence of these parasites in human pathology has created an increasing interest on the part of researchers in the systematic, epidemiological, clinical, diagnostic and therapeutic fields.

At present, diagnosis is based on PCR tests from oligonucleotides determined according to the ribosomal DNA sequences, the sole sequences known in most of the microsporidians. With regard to therapy, it is limited to certain compounds such as albendazole and fumagillin.

These unicellular eukaryotes exhibit a unique invasion mechanism. The spore, which is the infectious stage, contains an extrusion apparatus constituted by a polar tube inserted at its anterior end in an anchorage disk. Under the effect of certain stimuli, which can be linked in vitro to a variation in the pH, osmolarity, or the presence of cations or anions, the polar tube is extruded by the microsporidian spore and traverses the plasma membrane of a cellular host. The sporoplasm, expelled via this tube, is thereby inoculated into the receptor cell. These invasive apparatus, specific to the microsporidians and unique in the world of living organisms is, therefore, of great interest from not only the fundamental point of view but also from the applied point of view for diagnostics and therapeutics.

To date, no complete sequence of proteins constituting this polar tube has been obtained. According to Weidner [3], the polar tube is constituted by a single 23-kDa protein in *Ameson michaelis*. More recently, in a microsporidian parasite of fish, *Glugea americanus*, a differential extraction of the proteins in the presence of a reducing agent (DTT) made it possible to demonstrate that a 43-kDa protein is constitutive of the polar tube but only a part of the N-terminal sequence of 16 amino acids was determined [4]. Production of polyclonal and monoclonal antibodies against the polar tube of various species [5, 6, 7] has also been performed, thereby demonstrating a possible protein heterogeneity of this structure.

SUMMARY OF THE INVENTION

This invention discloses purified complete microsporidian polar tube proteins and the proteins, the amino acid sequences of which are represented in the attached sequence listings as SEQ ID No: 1, SEQ ID No: 2, SEQ ID No: 3, SEQ ID No: 4, SEQ ID No: 5. The invention discloses the genes coding these proteins and their use in the field of diagnosis.

BRIEF DESCRIPTION OF THE DRAWINGS

Characteristics and advantages of the invention will become manifest from the examples below concerning the production of antibodies against the polar tube, cloning and sequencing of the genes coding for the microsporidian polar tube proteins in *E. cuniculi* and which refer to the attached drawings in which.

A: electrophoretic separation of the sporal proteins;

B: analysis by indirect immunofluorescence using polyclonal antibodies directed against the 55-kDa band separated by SDS-PAGE ($1/50^{th}$ dilution) on MRC-5 cells infested by *Encep[halitozoon cuniculi*; and C: immunoblot with the anti-55 kDa polyclonal antibodies ($1/5000^{th}$ dilution, track 1) and the monoclonal antibody Ec 102 ($1/10,000^{th}$ dilution, track 2).

Figure 2:
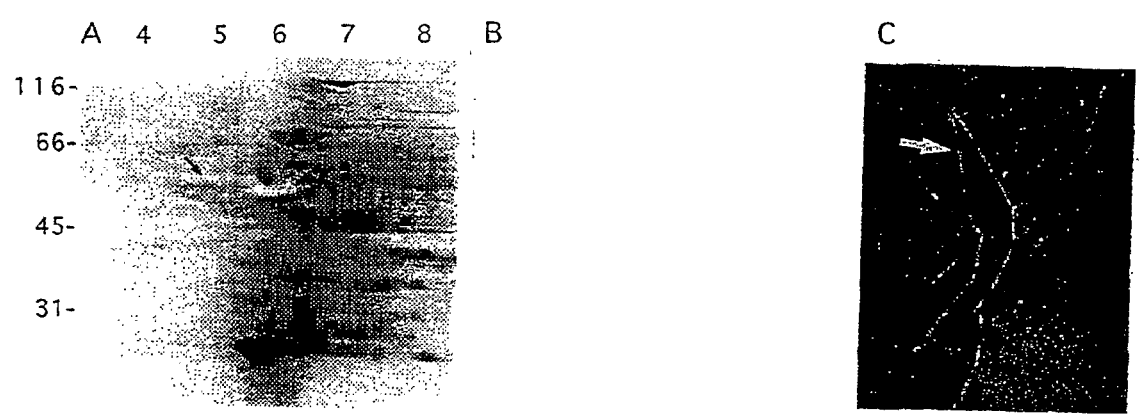

FIG. 2 shows the immunoreactivity of the 55-kDa protein.

Figure 3:
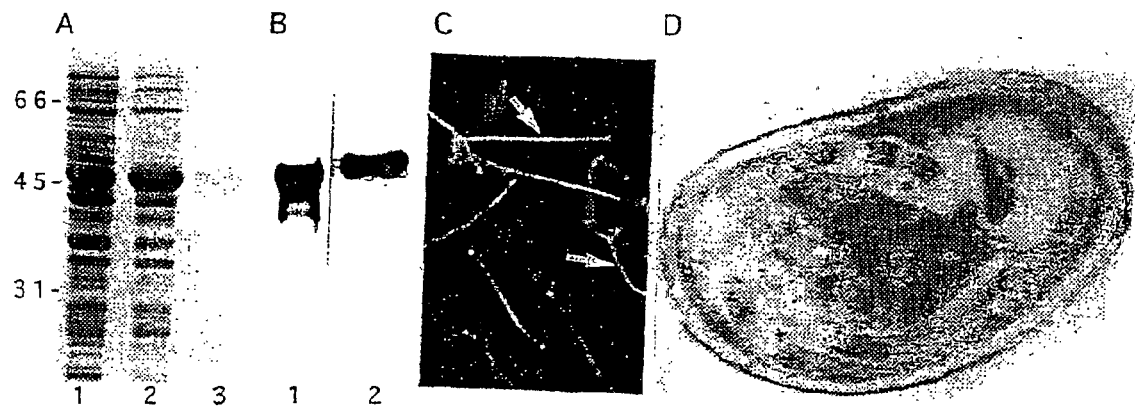

FIG. 3 illustrates the expression of PTP55 in *Escherichia coli*.

Figure 4:
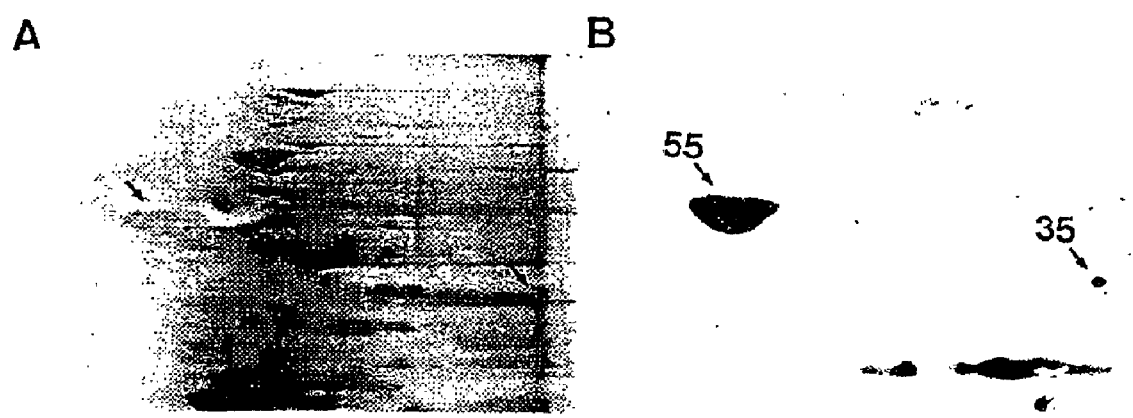

FIG. 4 shows an immunolabeling performed on two-dimensional electrophoresis gels with the monoclonal antibody directed against the polar tube.

Figure 5:
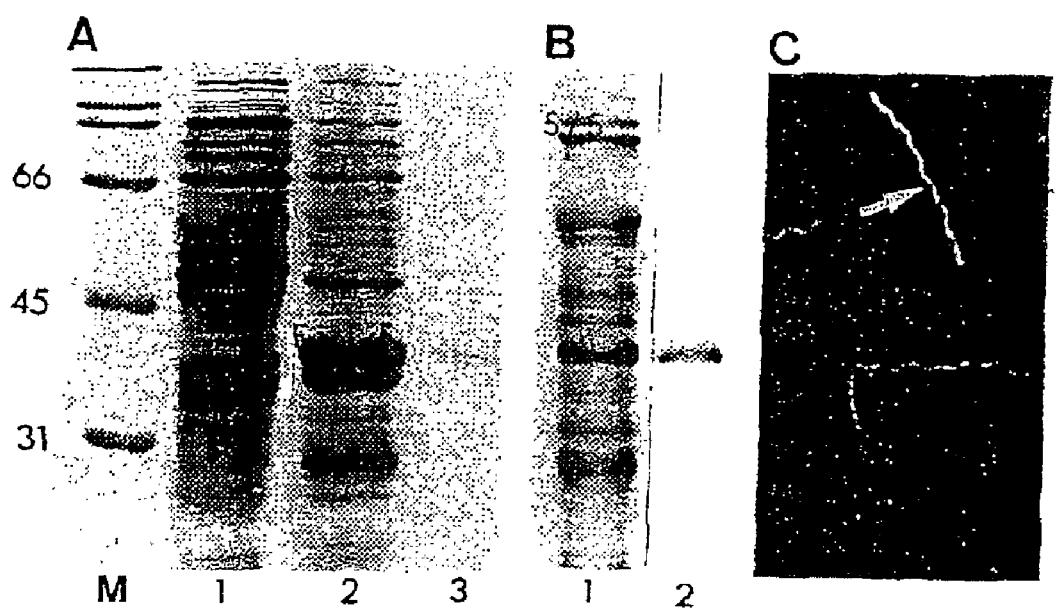

FIG. 5 illustrates the expression of PTP35 in *Escherichia coli*.

DETAILED DESCRIPTION

The research studies that led to this invention consisted first of all of producing polyclonal and monoclonal antibodies against the polar tube of *E. cuniculi*. We thereby obtained two polyclonal antibodies (anti-55 kDa and anti-35 kDa) and one monoclonal antibody (anti-55 kDa) which react specifically with the polar tube in immunofluorescence and in electron microscopy [6]. After separation of the sporal proteins by two-dimensional electrophoresis and transfer onto PVDF membrane, a protein with an apparent molecular weight close to 55 kDa and an isoelectric point of 5 was recognized by these three types of antibodies. On these two-dimensional gels, another protein of apparent molecular weight close to 35 kDa and with an isoelectric point of 9 was also recognized by two anti-polar-tube antibodies, the polyclonal anti-35 kDa antibody and the monoclonal antibody.

The research studies performed in the context of this invention, therefore, for the first time made it possible to obtain the complete polar tube proteins of microsporidians. (The studies presented by the inventors at a congress (Fifth International Workshops on Opportunistic Protists and Fifth General Meeting of the European Concerted Action on Pneumocystis Research, Lille, Sep. 3–7, 1997) on the production of a 55-kDa polar tube protein are insufficient to enable production of this complete and purified protein, and for the identification, cloning and sequencing of the corresponding gene. In fact, no nucleic or protein sequence data appear in the document recording this congress [8].)

The experimental protocol reported in that document comprises the conventional steps which are well known by those of ordinary skill in the art [9], such as extraction of the sporal proteins, electrophoreses (SDS-PAGE), production of polyclonal and monoclonal antibodies, microsequencing of peptides as well as the determination of degenerated primers and their amplification with PCR. In light of the synthetic character of the document recorded at the congress, its teaching is insufficient to allow one of ordinary skill in the art to reproduce the inventors' work and produce a complete sequence of a complete microsporidian polar tube protein.

Thus, an object of the invention is the complete purified polar tube proteins of microsporidians and, more particularly, of three microsporidian species of the genus *Encephalitozoon: E. cuniculi, E. intestinalis* and *E. hellem*. More particularly, the invention pertains to:

- a protein of apparent molecular mass of approximately 55 kDa and an isoelectric point on the order of 5 from *E. cuniculi* and *E. intestinalis*,
- a protein of apparent molecular mass of approximately 35 kDa and an isoelectric point on the order of 9 from *E. cuniculi, E. intestinalis* and *E. hellem.*

In a second stage, the studies performed on the two purified proteins from *E. cuniculi* (55 and 35 kDa) comprised subjecting them to internal microsequencing after digestion with Endolysine C. Two peptides were sequenced in this manner (P1: ATALCSNAYGLTPGQQGMAC (SEQ ID No: 6) and P2: SATQYAMEACATPTP (SEQ ID No: 7)) for the 55-kDa protein and one peptide (P3: AVQGTDRCILAGIID (SEQ ID No.: 8)) for the 35-kDa protein. It was possible using degenerated primers to amplify a part of the corresponding genes.

In the absence of a genomic library, we were able to determine the sequences of the genes and their flanking regions by means of an SSP-PCR technique [10]. As a result of these several stages of studies, it was possible to define the complete structure of the genes and their particularities as well as their possible similarities with other genes. The primary structures of the 55-kDa and 35-kDa proteins were also determined.

Thus, the invention pertains to the microsporidian polar tube proteins, the amino acid sequences of which are shown in the attached sequence listings as numbers SEQ ID No: 1, SEQ ID No: 2, SEQ ID No: 3, SEQ ID No: 4 and SEQ ID No: 5, a fragment or a functionally equivalent derivative thereof.

The phrase "functionally equivalent derivative" is understood to mean proteins, the sequences of which comprises a modification and/or a suppression and/or an addition of one or more amino acid residues, so long as this modification and/or suppression and/or addition does not substantially modify the function of these proteins. Such derivatives can be analyzed by one of ordinary skill in the art using the techniques of:

- screening expression libraries by means of antibodies directed against the polar tube proteins, or
- screening genomic libraries by means of nucleic probes capable of hybridizing with a gene coding for a polar tube protein.

The protein of 395 amino acids, referred to below as PTP55, represented in the attached sequence listing as SEQ ID No: 1 corresponds to the 55-kDa protein of *E. cuniculi*. It presents a deduced molecular weight of 36,609 Da and of 37,230 Da without the signal peptide, which is lower than that of 55,000 observed on polyacrylamide gels. This protein is synthesized by *E. cuniculi* in the form of a larger precursor the signal sequence of 22 amino acids of which is eliminated during screening towards the vesicles implicated in the formation of the polar tube. The sequence of a mature polar tube protein of the invention thus corresponds to the sequence comprised between the amino acids in positions 23 and 395 of SEQ ID No: 1. Various signal peptide characteristics can in fact be seen:

- predicted secondary structure forming an a helix,
- presence of hydrophobic amino acids as well as basic residues close to the N-terminal part,
- absence of a lysine residue in position 22, and
- prediction of signal peptide by von Heijne's algorithm [11].

In addition, the N-terminal sequencing of the protein demonstrated a sequence identical to that of the peptide P1, confirming that the peptide of 22 amino acids was cleaved upon maturation.

It can furthermore be seen that PTP55 does not contain tryptophan, phenylalanine or arginine residues. It presents a deduced isoelectric point of 4.7 in agreement with that seen on two-dimensional polyacrylamide gels which was on the order of 5. Investigation of these sequences of 395 amino acids and 373 amino acids in the mature protein shows that it does not present any significant homology with other proteins that have already been described in the databases.

A homologous protein of PTP55 was also identified in the species *E. intestinalis*. This protein of 371 amino acids is represented in the attached sequence listing as SEQ ID No: 3. The sequence presents notably strong homologies with the – and C-terminal regions of the PTP55 of *E. cuniculi*.

The protein of 277 amino acids, referred to below as PTP35, represented in the attached sequence listing as SEQ ID No: 2, corresponds to the 35-kDa protein of *E. cuniculi*. It presents a deduced molecular mass of 30,075 Da, thus smaller than that of 35,000 observed on polyacrylamide gels. The N-terminal end of PTP35 also presents signal peptide characteristics:

- predicted secondary structure forming an α helix,
- presence of hydrophobic amino acids as well as basic residues close to the N-terminal part,
- prediction of signal peptide by von Heijne's algorithm [11].

In the same manner as for PTP55, the PTP35 of *E. cuniculi* should present a signal peptide. Potential sites of proteolytic cleavage can be predicted between residues 12 and 13, 13 and 14 or 22 and 23. Nevertheless, such a cleavage could only be confirmed by the sequencing of the N-terminal part of the protein. On the basis of the available data, the sequence of a polar tube protein according to the invention is comprised between amino acids 1 and 277 of the sequence presented in the attachment as SEQ ID No: 2.

PTP35 does not contain tryptophan residues. It presents a deduced isoelectric point of 8.6 in agreement with that observed on two-dimensional polyacrylamide gels which was on the order of 9. Investigation of this sequence of 277 amino acids demonstrates that it does not present any significant homology with other proteins already described in the databases.

We also obtained homologous proteins of PTP35 in two other species of the genus *Encephalitozoon, E. intestinalis* and *E. hellem*. The corresponding sequences are attached as SEQ ID No: 4 and SEQ ID No: 5. The PTP35 of *E. intestinalis* and of *E. hellem* are constituted of 275 and 272 amino acids, respectively, and present approximately 80% identity. The sequence of a PTP35 polar tube protein of the invention corresponds more particularly to a sequence constituted by or comprising:

- the sequence comprised between the amino acids in positions 1 and 275 of the sequence represented in the attached sequence listing as SEQ ID No: 4, the sequence comprised between the amino acids in positions 1 and 272 of the sequence represented in the attached sequence listing as SEQ ID No: 5.

Polyclonal or monoclonal antibodies directed against at least one protein of the invention or a fragment thereof can be prepared by the methods described in the literature. The polyclonal antibodies are formed according to the conventional techniques by injection of the proteins, extracted from the spores of *E. cuniculi* or produced by transformation of a host, to animals, then recovery of the antiserums and of the antibodies from the antiserums by, for example, affinity chromatography. The monoclonal antibodies can be produced by fusing myeloma cells with spleen cells from animals that have previously been immunized with the proteins of the invention. These antibodies are useful for investigating other polar tube proteins of *E. cuniculi, E. hellem* or *E. intestinalis* and for studying the relationship between the polar tube proteins of different species or even different genera. In fact, the antibodies formed against the polar tube of *E. intestinalis* or *E. hellem* give rise to crossed immunological reactions with the polar tube proteins of *E. cuniculi*. But they can also find applications in the field of diagnostics.

The invention also pertains to a process for the diagnosis of infections caused by the microsporidians of the genus *Encephalitozoon* comprising the following steps:

a) a recombinant microsporidian polar tube protein according to the invention is immobilized on an analysis support such as a nitrocellulose film or an ELISA plate, b) the aspecific reaction sites are saturated, for example, in the presence of 5% skimmed milk, c) the product obtained in step (b) is incubated with the antibodies from the serum of the test subject in a manner such that if the serum contains antibodies directed against a microsporidian polar tube protein, they will complex with the protein, d) the antibodies that did not complex in step (c) are eliminated from the serum by washing, e) the product of step (d) is incubated with secondary antihuman antibodies coupled to a molecule enabling their visualization such as, for example, an enzyme such as peroxidase or a fluorochrome, f) the antihuman antibodies that are not specifically bound are eliminated by washing, and g) suitable means is used to visualize the antihuman antibodies/serum antibodies/protein complexes formed in step (e).

A diagnostic kit for the implementation of such a process is constituted by:

an analysis support on which the recombinant microsporidian polar tube proteins are immobilized, a solution containing antihuman antibodies coupled to a molecule enabling their visualization, and instructions regarding the steps of the diagnostic process described above.

The invention also pertains to a nucleic acid molecule comprising or constituted by a nucleic sequence coding for a microsporidian polar tube protein. More particularly, the invention pertains to the nucleotide sequences coding for the proteins of PTP55 and PTP35 corresponding to the 55-kDa and 35-kDa proteins, respectively, of the microsporidians *E. cuniculi, E. intestinalis* and *E. hellem*.

The invention envisages specifically a nucleic acid molecule comprising or constituted by a nucleic sequence coding for a microsporidian polar tube protein the amino acid sequence of which is represented in the attached sequence listing as SEQ ID No: 1, SEQ ID No: 2, SEQ ID No: 3, SEQ ID No: 4 or SEQ ID No: 5, a fragment or a functionally equivalent derivative of this protein.

A DNA molecule comprising the sequence coding for the protein PTP55 of *E. cuniculi* is represented in the attached sequence listing as SEQ ID No: 1 or its complementary sequence. More particularly, such a nucleic acid sequence comprises the sequence comprised between the nucleotides 411 and 1532 of SEQ ID No: 1 or its complementary sequence. The nucleic sequence of SEQ ID No: 1 is composed of 1830 nucleotides and an open reading frame of 1188 base pairs going from position 345 (ATG initiation codon) to position 1532 (TAG stop codon). The region preceding position 345 is susceptible of comprising elements that are useful for the transcription of protein PTP55 such as a promoter region.

A DNA molecule comprising the sequence coding for a homologue protein of PTP55 identified in the species *E. intestinalis* is represented in the attached sequence listing as SEQ ID No: 3.

A DNA molecule comprising the sequence coding for protein PTP35 is represented in the attached sequence listing as SEQ ID No: 2 or its complementary sequence. More particularly, such a nucleic acid sequence comprises the sequence comprised between nucleotides 458 and 1291 of SEQ ID No: 2 or its complementary sequence. Nucleic sequence II of the invention is composed of 1740 nucleotides and comprises an open reading frame of 834 base pairs going from position 458 (ATG initiation codon) to position 1291 (TAA stop codon). The region preceding position 458 is susceptible of comprising elements that are useful for the transcription of protein PTP35 such as a promoter region.

Two DNA molecules each comprising a sequence coding for a homologue protein of PTP35 in two other species of the genus *Encephalitozoon, E. intestinalis* and *E. hellem* are represented in the attached sequence listing as SEQ ID No: 4 and SEQ ID No: 5.

The invention thus concerns, most particularly, the nucleic acid molecules the nucleotide sequences of which are represented in the attached sequence listing as SEQ ID No: 1, SEQ ID No: 2, SEQ ID No: 3, SEQ ID No: 4 and SEQ ID No: 5 as well as nucleotide sequences capable of hybridizing with these molecules. The invention also concerns the nucleotide sequences derived from SEQ ID No: 1, SEQ ID No: 2, SEQ ID No: 3, SEQ ID No: 4 and SEQ ID No: 5, for example, due to the degeneration of the genetic code, and which code for the proteins presenting the characteristics of microsporidian polar tube proteins.

The invention also pertains to a vector comprising at least one of the preceding nucleic acid molecules, advantageously associated with adapted control sequences, as well as a process for the production or expression in a cellular host of a microsporidian polar tube protein of the invention or a fragment thereof. The preparation of these vectors as well as the production or the expression in a host of the proteins of the invention can be implemented by the molecular biology or genetic engineering techniques which are well known by the expert in the field.

As an example, a process for the production of a microsporidian polar tube protein according to the invention comprises:

transferring a nucleic acid molecule of the invention or a vector containing said molecule into a cellular host, culturing said cellular host under conditions enabling production of the microsporidian polar tube protein, isolating said proteins by any appropriate means.

As an example, a process for the expression of a microsporidian polar tube protein according to the invention comprises:

transferring a nucleic acid molecule of the invention or a vector containing said molecule into a cellular host, culturing said cellular host under conditions enabling expression of said proteins.

The cellular host employed in the preceding processes can be selected from among the prokaryotes or the eukaryotes, and especially from among the bacteria, yeasts, mammal cells, plant cells or insect cells. The vector employed is selected as a function of the host into which it will be transferred. It can be any vector such as a plasmid. The invention thus also pertains to the cellular hosts and, more particularly, to transformed bacteria such as *E. coli*, expressing the microsporidian polar tube proteins obtained in accordance with the preceding processes.

The invention also pertains to the nucleic probes and oligonucleotides prepared from the nucleic acid molecules of the invention. These probes, which are advantageously labeled, are useful for the detection by hybridization of similar sequences in other microsporidians. By means of the conventional techniques, these probes are brought into contact with a biological sample. Various hybridization techniques can be employed such as hybridization on blots (Dot-blot) or hybridization on replicas (Southern technique) or other techniques (DNA chips). Such probes constitute tools enabling rapid detection of similar sequences in the genes coding for the microsporidian polar tube proteins which makes it possible to study the origin and the conservation of these proteins constituting the polar tube.

The oligonucleotides are useful for PCR experiments, for example, for investigating the genes in other microsporidians or for diagnostic purposes.

The invention thus also pertains to a process for the diagnosis of infections caused by microsporidians, comprising the following steps:

a) the DNA is extracted from microsporidian spores taken from biological samples of urine, stool or a biopsy, b) the extracted DNA is amplified by any suitable means such as PCR with specific oligonucleotides deduced from the sequences of the genes coding for the microsporidian polar tube proteins, c) the amplification products are immobilized on an analysis support, d) the microsporidian origin of the amplification products is determined by hybridization by means of a labeled nucleotide probe specific to a microsporidian.

It is possible to perform step (c) by fixation of the amplification products on an analysis support such as a membrane or an ELISA plate.

A diagnostic kit for the implementation of such a process is constituted by:

the means required for the amplification of the sequences coding for the microsporidian polar tube proteins, such as the specific oligonucleotides of these sequences and all other elements necessary for the performance of a PCR, an analysis support for fixing the amplification products, and labeled probes specific to a microsporidian.

The invention also pertains to vaccinal compositions which prevent infections caused by the microsporidians of the genus *Encephalitozoon* comprising as active principle a protein of the invention or a fragment of the protein in association with a pharmaceutically acceptable vehicle. In fact, since the antibodies formed against the polar tube of *E. intestinalis* or *E. hellem* cause crossed immunological reactions with the polar tube proteins of *E. cuniculi*, the invention advantageously provides a potential vaccine against the infections caused by the microsporidians of the genus *Encephalitozoon*.

Figure 1:
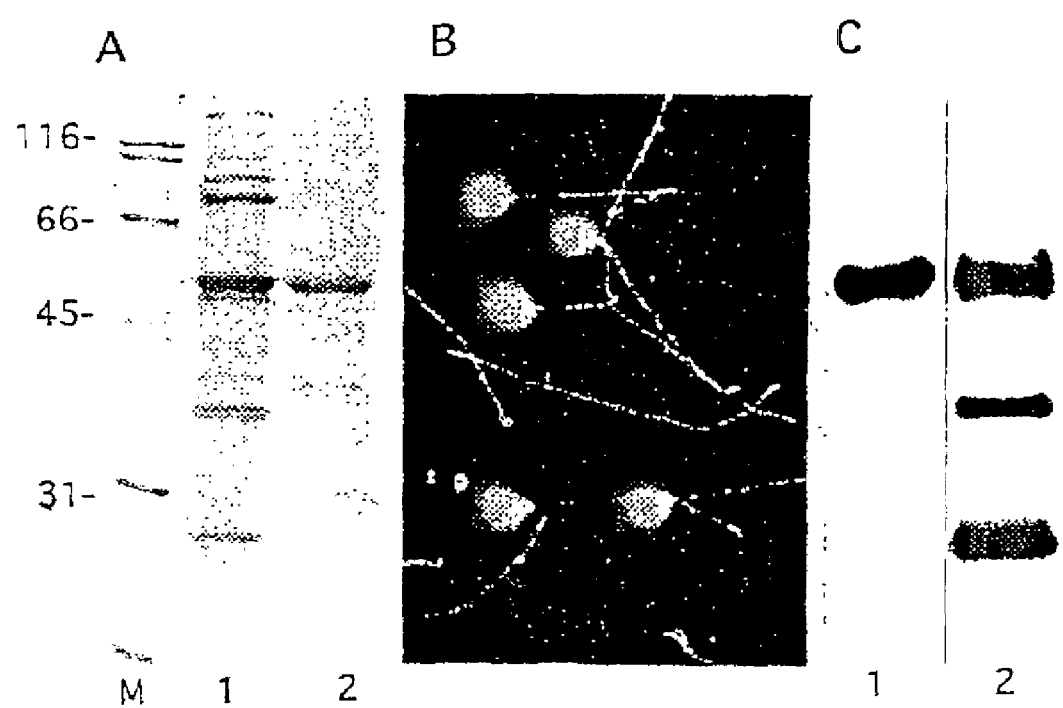
FIG. 1 shows.

Turning now to the drawings, FIG. 1 shows:

A: electrophoretic separation of the sporal proteins by SDS-PAGE with on track 1 the soluble fraction in 2% SDS, 10% 2-mercaptoethanol, and on track 2 the residual fraction obtained after incubation in 50% 2-mercaptoethanol for 48 hours.

B: analysis by indirect immunofluorescence using polyclonal antibodies directed against the 55-kDa band separated by SDS-PAGE ($1/50^{th}$ dilution) on MRC-5 cells infested by *Encephalitozoon cuniculi*. The spores with their extruded polar tubes are strongly marked.

C: immunoblot with the anti-55 kDa polyclonal antibodies ($1/5000^{th}$ dilution, track 1) and the monoclonal antibody Ec 102 ($1/10,000^{th}$ dilution, track 2). The molecular weight markers (M) are indicated on the left and given in kDa. The blots were visualized using an ECL kit (Amersham).

FIG. 2 shows the immunoreactivity of the 55-kDa protein. Two-dimensional gel electrophoresis was performed using isoelectrofocalization in the first dimension and 12 % gels in the second dimension. The separated proteins were either stained with silver nitrate (A) or transferred onto PVDF membranes and incubated with the polyclonal antibodies directed against the 55-kDa acid spot ($1/5000^{th}$ dilution) isolated by 2D electrophoresis (B). The molecular weights are indicated in kDa and the isoelectric points are numbered from 4 to 8. The specific labeling of the extruded polar tubes in immunofluorescence with this antibody can be seen in (C).

FIG. 3 illustrates the expression of PTP55 in *Escherichia coli*. A shows the analysis on polyacrylamide gels (SDS-PAGE) of the proteins extracted from bacteria transformed with the plasmidic construction pQE30-PTP55. Track 1 shows production without induction, track 2 shows the state after induction with IPTG and track 3 shows the recombinant PTP purified on Ni-NTA resin.

B shows an immunoblotting with the serums directed against the recombinant PTP55 ($1/1000^{th}$ dilution). On track 1, the *E. coli* proteins 4 hours after IPTG induction; on track 2, the proteins from *Encephalitozoon cuniculi*.

C shows a labeling with indirect immunofluorescence with the antiserums directed against the recombinant PTP55 of the polar tubes of *E. cuniculi*. The extruded polar tubes are indicated by arrows.

D shows an immunolabeling with colloidal gold in transmission electron microscopy of the polar tube sections.

FIG. 4 shows an immunolabeling performed on two-dimensional electrophoresis gels with the monoclonal antibody directed against the polar tube.

Two-dimensional gel electrophoresis was performed using isoelectrofocalization in the first dimension and 12% gels in the second dimension. The separated proteins were either stained with silver nitrate (A) or transferred onto PVDF membranes and incubated with the monoclonal antibodies ($1/5000^{th}$ dilution) (B). The 55-kDa and 35-kDa spots are indicated by arrows.

FIG. 5 illustrates the expression of PTP35 in *Escherichia coli*. FIG. 5 shows:

in A, polyacrylamide gel analysis (SDS-PAGE) of the proteins extracted from bacteria transformed with the plasmidic construction pQE30-PTP35. Track 1 shows production without induction, track 2 shows the state after induction with IPTG and track 3 shows the recombinant PTP purified on Ni-NTA resin. The molecular weight markers are indicated in kDa.

in B, an immunoblotting with the serums directed against the recombinant PTP35 ($1/1000^{th}$ dilution).

Track 1 shows the electrophoretic profile of *Encephalitozoon cuniculi* stained with Coomassie blue.

Track 2 illustrates the labeling of a 35-kDa protein from *E. cuniculi* with the antibody directed against the 35-kDa recombinant protein expressed in *Escherichia coli*.

in C, the indirect immunofluorescence labeling with the antiserums directed against the recombinant PTP35 of the polar tubes of *E. cuniculi*. The arrow indicates an extruded polar tube.

1) Production of Antibodies Against the Polar Tube of *E. cuniculi*, Immunocytochemical Analyses The strain of *E. cuniculi* employed was a mouse isolate. It was maintained in MDCK cellular culture. The spores released in the culture supernatant were recovered and stored at 4° C. in PBS. Extraction of the sporal proteins was performed by grinding the spores with zirconium balls (0.1 mm in diameter) in a buffer containing 2.5 % SDS and 10% 2-mercaptoethanol in the presence of protease inhibitors. After heat denaturation for 10 minutes at 100° C., the sporal debris was eliminated by centrifugation at 18,000 g for 5 minutes. The proteins were then separated by SDS-PAGE on 12% polyacrylamide gels.

For the two-dimensional electrophoresis, the protein samples were solubilized in a buffer based on 9 M urea, 5 % 2-mercaptoethanol and 40 mM CHAPS. Isoelectroocalization was performed under the following conditions: 4 hours at 400 V, 30 minutes at 600 V then 30 minutes at 800 V with the combination of 40% pH 3–10, 60% 4–6.5 ampholines (Pharmacia). After equilibration of the first-dimension gels in SDS/2-mercaptoethanol for 10 minutes, the proteins were separated according to their molecular mass by SDS-PAGE. The corresponding gels were dyed with either silver or Coomassie blue, or transferred onto PVDF membrane (Immobilon P, Polylabo) using a semi-dry system.

Polyclonal antibodies were produced against various *E. cuniculi* proteins separated by electrophoresis. Intraperitoneal injections were performed in BALB/c mice for each protein sample. The 55-kDa protein band was also used to produce monoclonal antibodies. Thus, three antibodies directed against the polar tube were obtained: two anti-35-kDa and anti-55-kDa polyclonal antibodies and one anti-55-kDa monoclonal antibody.

Immunoblotting, immunolocalization in IFA and in transmission electron microscopy were performed using conventional techniques.

2) Microsequencing PTPs of Apparent Molecular Masses 55 kDa and 35 kDa

The N-terminal sequence as well as two internal peptides (P1 (SEQ ID No: 6) and P2 (SEQ ID No: 7)) were sequenced for the PTP55 of *E. cuniculi*.

N-terminal: ATALCSNAYG (SEQ ID No: 9)
P1: ATALCSNAYGLTPGQQGMAQ (SEQ ID No: 6)
P2: SATQYAMEACATPTP (SEQ ID No: 7)
One internal peptide (P3) was sequenced for the PTP35.
P3: AVQGTDRCILAGIID (SEQ ID No: 8)

These sequences were performed on the 55-kDa and 35-kDa proteins isolated by two-dimensional electrophoresis, by the Protein Microsequencing Laboratory, Institut Pasteur, Biotechnology Department.

For the internal sequencing of the peptides P1 (SEQ ID No: 6), P2 (SEQ ID No: 8) and P3 (SEQ ID No: 7), the proteins were first digested by Endolysine C, proteolytic enzyme cutting after a lysine residue.

3) PCR Amplification, Cloning and Sequencing of the Genes Coding for the PTPs a) Genes Coding for the PTP55 of *E. cuniculi* and *E. intestinalis*

From degenerated primers deduced from the peptides P1 and P2, a DNA fragment of approximately 1 kpb was amplified, cloned in a plasmidic vector pCR2 (Invitrogen, TA cloning vector) and sequenced according to Sanger's method [12]. Amplification of the 5' and 3' regions of the gene of the PTP was performed by a PCR technique (SSP-PCR). Analysis of the sequences was performed on the molecular biology server Infobiogen.

The complete sequence represented in the attached sequence listing as SEQ ID No: 1 comprises 1830 nucleotides and has a reading frame of 1188 pb. This frame contains 395 codons going from the site considered to be the translation initiation site to the TAG termination codon. The codon considered to be the ATG departure codon is preceded by a region that is particularly rich in A-T. The translated amino acid sequence is represented in the attached sequence listing as SEQ ID No: 1.

By means of PCR and SSP-PCR amplifications, the gene coding for a homologous protein of PTP55 was sequenced and is represented in the attached sequence listing as SEQ ID No: 3. This sequence comprises a reading frame of 1113 pb. This frame contains 371 codons going from the site considered to be the translation initiation site to the TAG termination codon.

b) Genes Coding for the PTP35 of *E. cuniculi*, *E. intestinalis* and *E. hellem*

From degenerated primers deduced from the peptide P3 (SEQ ID No: 8), different fragments were amplified by the SSP-PCR technique, cloned in a plasmidic vector pGEMT (Promega, TA cloning vector), sequenced according to Sanger's method and analyzed as described above.

The complete sequence of the PTP35 of *E. cuniculi* represented in the attached sequence listing as SEQ ID No: 2 comprises 1740 nucleotides. The reading frame comprises 834 pb. This frame contains 277 codons going from the site considered to be the translation initiation site to the TAA termination codon. The codon considered to be the ATG departure codon is preceded by a region that is particularly rich in A-T, similar to that of PTP55. The translated amino acid sequence is represented in the attached sequence listing as SEQ ID No: 2.

The sequences of the PTP35 of *E. intestinalis* and *E. hellem* represented in the attached sequence listing as SEQ ID No: 4 and SEQ ID No: 5 contain, respectively, 825 and 816 nucleotides not including the stop codon. The corresponding proteins are constituted by 277 and 272 amino acids.

4) Expression of the PTPs in *Escherichia coli*

A part of the PTP55 of *E. cuniculi* corresponding to the region between the peptides P1 (SEQ ID No: 6) and P2 (SEQ ID No: 7) was cloned in an expression vector pQE30 (Qiagen) and expressed in *E. coli* (strain M15). The recombinant protein was purified by affinity chromatography on nickel columns and injected in mice. The corresponding antibodies tested in immunoblotting, immunofluorescence and transmission electron microscopy made it possible to confirm that this protein was in fact localized at the level of the *E. cuniculi* polar tube.

A part of the PTP35 between the residues 27 and 277 of (SEQ ID No: 2) was also expressed in *E. coli* using the same technique. The antibodies produced against this recombinant protein exhibited a labeling of the polar tube.

5) Analysis of the Primary Sequences of the PTP55 and PTP35

Blast analysis did not reveal any significant homology with other known proteins with the exception of collagen, principally due to the fact that PTP55 is rich in glycine and proline residues.

a) The PTP55 are rich in proline, glycine, glutamine, serine and threonine residues with these five accounting for more than 55 % of the amino acid content. The proposed cleavage site (between the serine and alanine residues of the PTP55 of *E. cuniculi*) is predicted as such by the following characteristics:

- absence of lysine residue in position 22 preceding the P1 peptide (23–42) sequenced after digestion of the protein with Endolysine C,
- N-terminal sequencing of the protein corresponding to that of the peptide P1,
- presence of hydrophobic amino acids in this N-terminal region,
- von Heijne's algorithm,
- secondary structure in α helix.

The PTP is most likely synthesized by *E. cuniculi* (or *E. intestinalis*) in the form of a larger precursor the 22-amino-acid signal sequence of which is eliminated upon maturation. The mature protein would, therefore, have a molecular mass of 37,230 Da.

N-glycosylation sites (NETS, NGTS and NISG) are present in the sequence. The presence of numerous serine and threonine residues (21.6%) is also suggestive of O-glycosylation sites.

The central region of the protein PTP55 of *E. cuniculi* is characterized by four repetitions in tandem of 26 amino acids, each with a conservation at the nucleic level. This region is partially framed by two other repetitions of 9 amino acids. No repetition was seen in the PTP55 sequence of *E. intestinalis*, but the two PTP55 present strong homologies in the N-terminal and C-terminal parts.

b) The PTP35 are particularly rich in lysine residues (11.5%) and glutamic acid (9%). Three potential cleavage sites of a signal sequence are represented between the residues 12 and 13, 13 and 14, and 22 and 23. An RGD sequence is present in the PTP35 of *E. cuniculi* and *E. intestinalis*; this sequence is also found in proteins such as fibronectin and intervenes in cellular attachment phenomena. A potential N-glycosylation site (NSTS) is also present in the PTP35 sequence of *E. cuniculi*.

6) Chromosomal Localization and Estimation of the Number of Copies

Hybridization of a probe corresponding to a part of the gene coding for PTP55 on the chromosomes of *E. cuniculi* separated by pulsed field electrophoresis revealed a unique localization of this gene on chromosome VI.

The same probe was applied on Southern blots after digestion of the genomic DNA of *E. cuniculi* by different restriction enzymes: a single band is marked on each digestion profile which makes it possible to affirm that the gene exists in a single copy.

The gene coding for the PTP35 of *E. cuniculi* is also localized on chromosome VI.

Bibliographic References

1) Desportes-Livages, Parasite (1996) 3: 107–113.
2) Van Gool et al., J Infect Dis (1997) 175: 1020–1024.
3) Weidner, J Cell Biol (1976) 71: 23–34.
4) Keohane et al., Mol Biochem Parasitol (1996) 79: 255–259.
5) Beckers P. J. A. et al., J Clin Microbiol (1996) 34: 282–285.
6) Delbac et al., J Euk Microbiol (1998) 45: 224–231.
7) Keohane et al., J Euk Microbiol (1996) 43: 26–31.
8) Delbac et al., J Euk Microbiol (1997) 44: 77S.
9) Watson et al., ADN recombinant [Recombinant DNA], Ed Brussels (1994).
10) Shyamala and Ames, Methods Enzymol (1993) 217: 436–446.
11) Von Heijne, Nucl Acids Res (1986) 14: 4683–4690.
12) Sanger et al., Proc Natl Acad Sci USA (1977) 74: 5463–5467.
13) Land et al., Parasitology Today (1995) 11: 19–23.

What is claimed is:

1. An isolated microsporidian polar tube protein consisting of the sequence between amino acids 23 and 395 of SEQ ID No: 6.

2. An immunogenic composition comprising the isolated microsporidian polar tube protein of claim 1 and a pharmaceutically acceptable carrier.

3. The composition of claim 2, wherein said composition forms antibodies against at least one polar tube selected from the group consisting of *E. intestinalis, E. cuciculi* and *E. hellem.*

4. The composition of claim 2, wherein an antibody has a crossed immunological reaction with the polar tube protein of SEQ ID No: 6.

* * * * *